United States Patent [19]

Burnett, Jr. et al.

[11] Patent Number: 4,865,982
[45] Date of Patent: Sep. 12, 1989

[54] CLONED STREPTOMYCETE GENE

[75] Inventors: William V. Burnett, Jr., Syracuse, N.Y.; Thomas G. Eckhardt, Collegeville; Louis R. Fare, Lafayette Hill, both of Pa.

[73] Assignee: SmithKline Beckman Corporation, Philadelphia, Pa.

[21] Appl. No.: 738,814

[22] Filed: May 29, 1985

Related U.S. Application Data

[63] Continuation-in-part of Ser. No. 586,536, Mar. 5, 1984, abandoned, which is a continuation-in-part of Ser. No. 384,650, Jun. 3, 1982, abandoned.

[51] Int. Cl.[4] .................. C12N 1/20; C12N 15/00; C12N 1/00
[52] U.S. Cl. .................. 435/252.35; 435/172.3; 435/320; 935/11; 935/48; 935/41
[58] Field of Search .................. 435/172.3, 253, 317; 935/9, 11, 41, 43, 48

[56] References Cited

U.S. PATENT DOCUMENTS 3,816,259  6/1974  Collinge et al. ............... 435/207
4,717,666  1/1988  Brawner et al. ............... 435/253

FOREIGN PATENT DOCUMENTS 2033905  5/1980  United Kingdom .

OTHER PUBLICATIONS

Altenbuchner et al., Mol. Gen. Genet., vol. 195, pp. 134–138, Jun. 4, 1984.
Kieser, Plasmid, vol. 12, pp. 19–36, 1984.
Ross et al., J. of General Microbiology, vol. 127, pp. 339–350 (1981).
Bibb et al., Nature 284:526–531 (1980).
Thompson et al., Nature 286:525–527 (1980).
Davis et al., Nature 283:433–438 (1980).
Villa-Komaroff et al., Proc. Nat'l Acad. Sci., U.S.A. 75:3727–3731 (1978).

*Primary Examiner*—Alvin E. Tanenholtz
*Attorney, Agent, or Firm*—Edward T. Lentz; Janice E. Williams; Alan D. Lourie

[57] ABSTRACT

A DNA fragment from *Streptomyces sp.* which contains the XP55 gene expression unit.

10 Claims, 1 Drawing Sheet

CLONED STREPTOMYCETE GENE

This is a continuation in part of U.S. patent application Ser. No. 586,536, filed Mar. 5, 1984, now abandoned, which is a continuation in part of U.S. patent application Ser. No. 384,650, filed June 3, 1982, now abandoned.

FIELD OF THE INVENTION

This invention relates to the field of biotechnology, specifically to genetic engineering. More particularly, the invention relates to the cloning of a gene coding for an exported protein from a Streptomyces species onto suitable vectors, expression of such cloned gene in other Streptomyces species and the use of such cloned gene for various genetic engineering purposes.

BACKGROUND INFORMATION

Although the Actinomycetales produce more than half of the known antibiotics having valuable clinical and other applications as secondary metabolites and, thus, are recognized as a key target for application of gene manipulation techniques, many problems remain to be overcome before specific useful genes are successfully identified and cloned ["Molecular Breeding and Genetics of Applied Microorganisms", Sakaguchi and Okanishi, eds., Academic Press (New York) Kodansha Ltd. (Toyko) 1980, pgs. 130–131]. Until the present work, cloning of a β-galactosidase gene from a Streptomyces species onto a suitable vector followed by introduction and expression of such vector has not been reported. Prior work has concerned development of other cloning systems or vectors for Streptomycetes [Bibb et al. (1978), *Nature* 274: 398–400; Hayakawa et al. (1979), *J. Antibiot.* XXXII(12): 1348–1350; Okanishi et al. (1980), *J. Antibiot.* XXXIII(1): 88–91; Bibb et al. (1980), *Nature* 284: 526–531; Thompson et al. (1980), *Nature* 286: 525–527; Suarez et al. (1980), *Nature* 286: 527–529; Bibb et al. (1981), *Mol. Gen. Genet.* 184: 230–240]; Bibb (1981), "Microbiology-1981", Schlessinger, ed., American Society for Microbiology, (Washington, D.C.) 1981, pgs. 367–370 and Hopwood et at. (1981), "Microbiology-1981", supra. pgs. 376–379], cloning and expression in Streptomyces sp. of genes derived from *Escherichia coli* [Schottel et al. (1981), *J. Bacteriol.* 146: 360–368] and cloning of genes from Streptomycetes in *Escherichia coli* ["Molecular Breeding and Genetics of Applied Microorganisms", supra; pgs. 130–137]. Chater et al. (1982), *Current Topics in Microbiol. and Immunol.* 96: 69–95, review gene cloning in Streptomyces and is incorporated by reference herein as though fully set forth.

SUMMARY OF THE INVENTION

One aspect of the invention is a DNA fragment comprising the XP55 gene expression unit.

Another aspect of the invention is a DNA fragment comprising the XP55 gene promoter.

Another aspect of the invention is a fused gene comprising an excretion signal from the gene of the invention, that is, the whole coding sequence or a portion thereof, fused to a heterologous coding sequence.

Other aspects of the invention include vectors containing said fragments and microorganisms transformed therewith.

All of these embodiments of the invention, as well as others described herein, are readily attainable uses of this invention and are considered as further aspects of the same invention.

DISCLOSURE OF THE INVENTION

Figure 1:
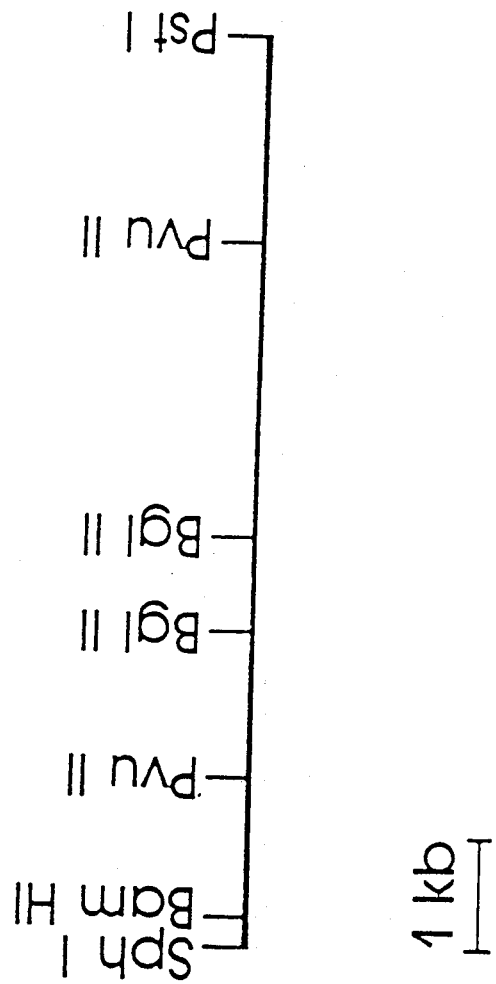
FIG. 1 is a restriction endonuclease cleavage map of pSKL-1.
Figure 2:
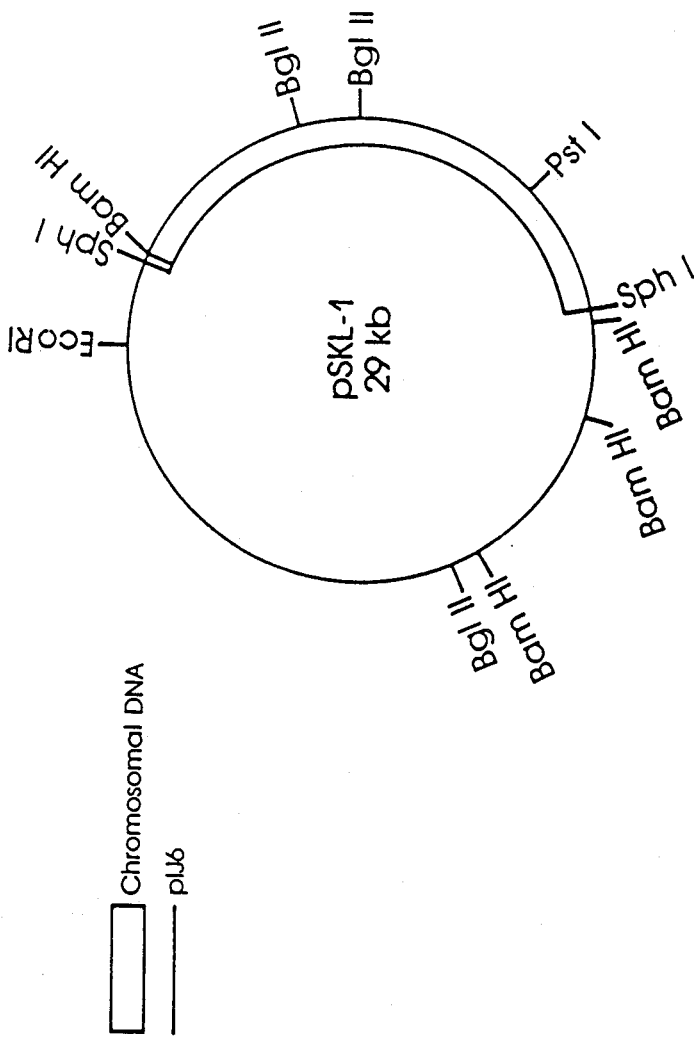

XP55 is a protein naturally expressed and exported by Streptomyces. Its function is not understood. The present utility of the XP55 gene expression unit is as a source of a useful Streptomyces promoter, the XP55 gene promoter, which may be referred to as the P2 promoter, and as a source of an excretion signal for export of heterologous, fusion proteins.

Described below are various DNA fragments of Streptomyces origin which have been discovered to carry the XP55 gene expression unit. It is appreciated that derivatives of the disclosed fragments may also carry a XP55 gene expression unit. Such derivatives are included within the invention. Moreover, it is understood that fragments similar to those disclosed herein, such as fragments differing by the presence or absence of one or more deoxyribonucleotides, including, perhaps, one or more restriction enzyme sites, which differences do not materially affect the biological function of the fragments, for example, gene expression and export, are included within the invention.

The DNA fragments of the invention are recombinant DNA molecules, that is, DNA sequences, single or double stranded, that have been isolated from the larger molecules in which they are naturally present, such as chromosomal DNA, or from their natural hosts, or which have been partially or wholly synthesized, and which may be fused to other DNA fragments, such as to form expression units or cloning or expression vectors.

The XP55 gene expression unit has been found to be located just upstream of the gene for the Streptomyces β-galactosidase and just downstream of the P49 gene expression unit in *S. lividans* strain 1326. P49 is a putative protein having a molecular weight of about 49,000. The Streptomyces β-galactosidase and P49, referred to as the Bgl protein, are the subject matter of copending patent applications.

The Streptomyces β-galactosidase gene, that is, the gene which causes expression of the Streptomyces β-galactosidase, is naturally present in and was originally isolated from a 16 kb Sph I region of chromosomal DNA of *S. lividans* strain 1326, which region also carries the P49 and XP55 gene expression units. The Sph I region has been mapped substantially as follows:

| Restriction Enzyme | Location (kb) |
| --- | --- |
| Sph I | 0 |
| Bam HI | 0.6 |
| Pvu II | 0.9 |
| Bal I | 1.3 |
| Stu I | 1.5 |
| Sal I | 1.8 |
| Stu I | 1.9 |
| Bcl I | |
| Bgl II | 2.7 |
| Bgl II | 3.7 |
| Pvu II | 5.7 |
| Nru I | 6.5 |
| Pvu II | 7.2 |
| Bcl I | |
| Stu I | 7.7 |

| Restriction Enzyme | Location (kb) |
| --- | --- |
| Pst I | 8.8 |
| Bal I | 9.1 |
| Pvu II | 10.3 |
| Pvu II | 10.9 |
| Bam HI | 11.6 |
| Stu I | 12.0 |
| Bcl I | 13.0 |
| Pvu II | 13.7 |
| Sph I | 15.5 |

This table will be used for further references herein to DNA fragments naturally present within the Sph I region. So, for example, the 1.0 kb Bgl II (2.7)–Bgl II (3.7) fragment will be referred to as such whether or not there are additional deoxyribonucleotides upstream and/or downstream thereof.

The entire XP55 gene expression unit can be obtained by restricting chromosomal DNA with Bgl II (partial) and Pvu II and selecting for the 3 kb Bgl II (2.7)–Pvu II (5.7) fragment. It, or other fragments of this region of chromosomal DNA, can be cloned in a vector, such as a phage or plasmid, by known techniques. Alternatively, by way of example, all or part of the gene expression unit can be sequenced and parts thereof can be synthesized. These can be used directly as regulatory or coding sequences or to construct other fragments such as hybrid promoters or hybrid coding sequences or to probe for similar regions in other organisms by standard hybridization techniques.

The locations of functions within the Sph I region provided below are approximate. The XP55 promoter begins in the region between the Bgl II sites, after the upstream coding sequence for the Bgl protein. Based on S1 mapping, it appears that the transcription start site is about 250–260 bases upstream (3') of the Bgl II (3.7) site. Based on DNA sequence data, on analysis of open reading frames and on molecular weight of XP55, it appears that the translation start site is about 30 bases farther downstream at an ATG codon.

The promotor region can be isolated from the Bgl II region by restriction with Bgl II. Such Bgl II fragment can be cut back from the 3' end to remove XP55 coding sequences to prepare a promoter having the XP55 translation start site, the XP55 Shine-Dalgarno sequence, and/or the XP55 transcription initiation site. Such Bgl II fragment can also be cut back from the 5' end to remove upstream sequences. Removal of a large number of 5' non-coding sequences reduces promoter efficiency. For expressing heterologous proteins from non-Streptomyces, it may prove desirable to include a N-terminal coding sequence of Streptomyces origin, such as the coding sequence for the first 30–40 amino acids of XP55 which sequence can be useful in transport of the protein to or beyond the membrane.

The coding sequence can be isolated from the 16 kb Sph I region by restriction with Bgl II (partial) and Pvu II to isolate the 3 kb Bgl II (2.7)–Pvu II (5.7) fragment. Sequences between the translation start site and near the Bgl II (3.7) site, including, for example, sequences in the Bgl II (2.7)–Pvu II (5.7) region, are involved in excretion. Such sequences can be isolated by known techniques such as disclosed by Silhavy et al., U.S. Pat. No. 4,336,336 for fusion to heterologous, that is, non-XP55, coding sequences for proteins which are normally not excreted and linked in phase to a promoter for expression of an excreted fusion protein. The XP55 export signal has not been conclusively identified. A single N-terminus of the protein has not been observed. Three N-terminal amino acids, pro, asp and glu, have been observed. Ala-cys, such as occurs at positions 33 and 34, have been reported as processing sites for outer membrane proteins.

The sequence of an illustrative DNA fragment of the invention from upstream of the promoter through the XP55 gene expression unit, isolated from *S. lividans* strain 1326 chromosomal DNA, follows.

```
                              CCGGCATCAC CCTCGTCCAG GGCGCGACAT CACCCGCCAG
AGCGCCGACG TGATCGTCAA CGCCGCCAAC TCCTCGCTCC TCGGCGGAGG CGGTGTCGAC GGCGCCATCC
ACCGACGCGG CGGCCCCGCG ATCCTGGCGG AGTGCCGCAG GCTCCGCGCG GTCACCTCG GCAAGGGCCT
GCCCACGGGC CGTGCGGTCG CCACCACCGC GGGCGACCTG GACGCGCGCT GGGTGATCCA CACGGTCGGC
 CCGGTCTGGT CGGCCACCGA GGACCGCTCC GGCCTCCTCG CCTCCTGCTA CCGCGAATCC CTGCGCACCG
 CCGACGAGTT GGGCGCCCGC ACGGTGGCCT TCCCCGCCAT CTCCACCGGC GTCTACCGCT GGCCGATGGA
CGACGCGGCC CGCATCGCCG TCGAGACGGT GGCGACCAGC GGGACCTCGG TGACCGAGGT CCGCTTCGTC
CTCTTCGATG CCCGGGCGTA CGAGGCGTTC GCGGCGCGGC TGGGCTGAGC ACCGCAGGCG CCCCGCCCGG
  TAACGGCCGA CCCGCTGCGC CGGCACCCTC CCCACCTGGC TTGACGCTTT ATTGCGAGTG ATGTGCAATA

GCTGCGCATC GACAACAAGC GTGGGGGAGA C ATG ACA GCC CGT CGG ACC CGT TGG ACC
                                        MET Thr Ala Arg Arg Thr Arg Trp Thr

CGT CGG ACC GAC CGG AGC CTT CCG ATA CGG AGT GCC GCC GCC GCG GTG GCG TTC
      Arg Arg Thr Asp Arg Ser Leu Pro Ile Arg Ser Ala Ala Ala Ala Val Ala Phe

GCC GCC GGT GCG ACC GCC TGC TCC GCG CCC ACG GGC GGC GGA GGG GAC GGC GGC
      Ala Ala Gly Ala Thr Ala Cys Ser Ala Pro Thr Gly Gly Gly Gly Asp Gly Gly

ACC GAG GCG GCC GAA TCC GTC GTC ATC GGC GTG GCC TCG GAA CCG GAC ACC CTC
      Thr Glu Ala Ala Glu Ser Val Val Ile Gly Val Ala Ser Glu Pro Asp Thr Leu

AGC CCG CTG CTC GGC TAC GGC AAG GAC GGA AAC TCC AAG ATC TTC GAC GGG CTG
      Ser Pro Leu Leu Gly Tyr Gly Lys Asp Gly Asn Ser Lys Ile Phe Asp Gly Leu
                                                         |
                                                       Bgl II

CTC GCC CGC GAC ACC GAC CTG GAG CTG AAG CCC GCC CTC GCC GCC GCG CTG CCG
      Leu Ala Arg Asp Thr Asp Leu Glu Leu Lys Pro Ala Leu Ala Ala Ala Leu Pro

AAG GTC ACC GAC GAC GGC CGC ACG ATC ACG TTC ACC CTG CGC GAG GGC GTG AAC
      Lys Val Thr Asp Asp Gly Arg Thr Ile Thr Phe Thr Leu Arg Glu Gly Val Asn
```

-continued

```
TTC AGC GAC GGC GAA CCG CTG ACG GCG GGG GAC GTC TAC ACG TAC CGC ACC GTC
Phe Ser Asp Gly Glu Pro Leu Thr Ala •Gly Asp Val Tyr Thr Tyr Arg Thr Val

CTC GAC GAG AAG ACC AAC AAC ACC GCC CGC AGC GAA CTC GAC GCC GTT CGA GAA
Leu Asp Glu Lys Thr Asn Asn Thr Ala Arg Ser Glu Leu Asp Ala Val Arg Glu

CGT TCC GCG CGA GCG GAC GGC ACC GTC GTC TTC ACC CTC AAG TAC CCT TAC GCG
Arg Ser Ala Arg Ala Asp Gly Thr Val Val Phe Thr Leu Lys Tyr Pro Tyr Ala

CCC TTC GCC GCC CGC ACC GTC CTG CCC ATC GTC CCC GAG CAC GTC GCC GGG AAG
Pro Phe Ala Ala Arg Thr Val Leu Pro Ile Val Pro Glu His Val Ala Gly Lys

CAG GAC CCC AAC ACC GGC GAC TTC AAC ACC GAG CCG GTC GGC ACC GGA CCG TAC
Gln Asp Pro Asn Thr Gly Asp Phe Asn Thr Glu Pro Val Gly Thr Gly Pro Tyr

GTG CTC ACC GGC TGG AGC AAG GGC GAG AAG CTC GGC TTC AGG GCC AAC CCG CAC
Val Leu Thr Gly Trp Ser Lys Gly Glu Lys Leu Gly Phe Arg Ala Asn Pro His

XmnI
                                                        |
              TAC TGG GGC GAC AAG CCC GCG GTG AAG TCG TTC ACC ATG GCC GTC ACC
              Tyr Trp Gly Asp Lys Pro Ala Val Lys Ser Phe Thr Met Ala Val Thr
```

In an illustrative procedure, *Streptomyces lividans* strain 1326 [National Collection of Industrial Bacteria, Aberdeen, Scotland, number 11416; Bibb et al., (1981), *Mol. Gen. Genetics* 184: 230-240; Krasilnikov et al., "The Biology of Certain Groups of Actinomycetes", Krasilnikov, ed., Science Press (Moscow) 1965, pgs. 109-110]; which contains a gene which codes for β-galactosidase which is naturally excreted in its original strain, is collected by standard techniques, such as the technique described by Chater et al., supra. A DNA fragment containing the gene which codes for an excretable β-galactosidase is isolated by treating the DNA with a restriction endonuclease. If the enzyme-substrate reaction yields a poorly diffusible dye, enzymatic activity can be monitored by the formation of a halo of colored dye around a producing colony on an agar plate when assaying by this procedure. The preferred chromogenic substrate is X-gal because the product is such a poorly diffusible dye. The sensitivity of this procedure is such that one producing colony among 300 to 500 colonies can be identified on a single petri dish (90 mm diameter).

The genes isolated as described above, and which originated from Streptomyces, can be readily expressed in other species of Streptomyces such as *Streptomyces griseus, Streptomyces aureofaciens, Streptomyces fradiae, Streptomyces niveus* and others as well as other microorganisms. *Streptomyces lividans, Streptomyces albus* and *Streptomyces griseus* are the preferred host species.

A variety of vectors are useful in this invention, the choice of an advantageous one being within the ken of one skilled in the relevant art. Examples of usable vectors are plasmids pIJ6 [Thompson et al. (1980), *Nature* 286: 525-527], pIJ101 [Chater et al. supra] and others which are capable of replicating in the ultimate host strain and permit facile selection for the presence of the vector in such strain. Likewise, various standard growth media can be employed. The plasmid, pIJ6, is the preferred vector.

Incorporation of a plasmid vector containing the desired DNA fragment into microorganisms can be accomplished by usual transformation methods, although other procedures such as transduction or conjugation may be used with suitable hosts. Such procetures are described in and known to the art.

The following examples are intended to provide a detailed description of the present invention and manner of carrying it out, but not to limit its scope, applicability or utility.

EXAMPLE 1

Chromosomal DNA from *Streptomyces lividans* strain 1326 [Bibb et al. (1981), supra.] was isolated using the procedure described by Chater et al, supra. Plasmid pIJ6 isolated from *Streptomyces lividans* [*Thompson et al.* (1980), supra.] was used as the cloning vector as this plasmid carries the gene for thiostrepton resistance, which is useful as a selective marker to select for the plasmid in a given thiostrepton sensitive strain such as 1326 and its derivatives. Treatment of the chromosomal DNA and the pIJ6 DNA with Sph I restriction endonuclease or Pst I restriction endonuclease yielded DNA fragments having a protruding complementary 3' DNA sequence. The pIJ6 DNA was additionally treated with alkaline phosphatase to prevent regeneration of the cloning vector without an additional DNA insert. The Sph I and the Pst I generated DNA's (5 ug of chromosomal DNA, 1 ug of pIJ6 DNA) were ligated separately at 16° C. for 7 days using standard procedures. The ligated DNA's were transformed substantially according to the procedure described by Chater et al., supra., using about $2 \times 10^7$ protoplasts derived from *Streptomyces lividans* strain 1326-9, a nitrosoguanidine induced mutant of strain 1326 lacking any excreted β-galactosidase activity. The protoplasts were spread onto regeneration medium plates and incubated for 18-24 hours at 28° C. The plates were overlaid with a soft agar mixture (0.4% agar in water) containing 100 ug/ml of thiostrepton to select for transformed offspring and 150 ug/ml of X-gal. The plates were incubated for another 2 to 6 days at 28° C., then scored for the appearance of characteristic blue colonies.

Of over 10,000 thiostrepton resistant colonies resulting from the Sph I cloning, 9 turned blue; from about the same number of colonies resulting from the Pst I cloning, one turned blue. The plasmid DNA of all the blue colonies was isolated and analyzed.

Both plasmid DNA from the Sph I and the Pst I cloning had one common 9 kilobase DNA fragment (Sph I (0)-Pst I (8.8)) derived from the chromosome and not previously present on the pIJ6 plasmid. Initially, it was believed, based on what was believed to be the structure of pIJ6, that said 9 kb region contained the Streptomyces β-galactosidase gene. The total Sph I insert was believed to comprise only about 10 kb. As shown in further examples below, it was subsequently discovered that although the gene is located on the Sph I insert, the Pst I-Sph I fragment is not the 9 kb fragment originally identified, but rather is a 6.5 kb fragment located downstream thereof.

A 32 kilobase plasmid derived from the Sph I cloning was termed "pSKL-1". Cleavage by the restriction endonucleases was carried out in the standard manner. The plasmid derived from the Pst I cloning was termed "pX". pSKL-1 is represented by the restriction endonuclease cleavage map shown in FIG. 1.

The isolated plasmid DNA from pSKL-1 was used to transform Streptomyces lividans 1326-9. Over 70% of the thiostrepton resistant offspring showed an excreted β-galactosidase activity, indicating the presence and expression of the gene on the plasmid. The enzyme levels of cell extracts of the pSKL-1 transformed strain, strain 1326-9/pSKL-1, were increased, in some cases, 100 times, thus showing the presence of the gene on the plasmid. Results of one experiment are given in Table 1, below.

TABLE 1

| STRAIN | β-GALACTOSIDASE ACTIVITY (nmoles/mg protein/min) CARBON SOURCE IN GROWTH MEDIUM | | |
|---|---|---|---|
| | GLUCOSE | LACTOSE | GALACTOSE |
| 1326 | 12 | 76 | 184 |
| 1326-9 | 7 | 24 | 302 |
| 1326-9/pSKL-1 | 372 | 843 | 1242 |

As indicated in Table 1, a few 1326-9 cultures produced more unexcreted β-galactosidase in the presence of galactose than some 1326 cultures.

Transformants harboring the pSKL-1 plasmid produced darker blue colonies than the original 1326 strains, demonstrating the utility of the DNA fragment containing the β-galactosidase gene in the construction of high expression vectors.

β-galactosidase expression from a plasmid is less stable in strain 1326-9 than in strain 1326. This is believed to be due to recombination with chromosomal DNA.

Transformants harboring pSKL-1 also showed, upon gel electrophoresis of proteins in the media, presence of XP55 which was not observed in strain 1326.

EXAMPLE 2

Plasmid pSKL-1 was also transformed into Streptomyces griseus strain BC6, ATCC No. 10137, a strain which naturally does not possess an excreted β-galactosidase or XP55, by the above described procedures. The offspring of strain BC6 containing pSKL-1 (strain BC6/pSKL-1), however, produced an excreted β-galactosidase and XP55, demonstrating the applicability and usefulness of the β-galactosidase gene in other Streptomycete hosts.

EXAMPLE 3

The Bgl II region of pSKL-1 was isolated and fused directly to a E. coli lacZ coding sequence, which included the lacZ Shine-Dalgarno sequence and translation initiation site, in a pIJ101 derivative and in a pBR322 derivative. The derivative plasmids were transformed into S. lividans strain 1326 and an E. coli which does not normally produce β-galactosidase, respectively. The resulting Streptomyces and E. coli transformants expressed the lacZ coding sequences resulting in production of the E. coli β-galactosidase in amounts of about 2–3% of total cellular protein.

The Bgl II region was similarly used to promote expression of an E. coli galK coding sequence in amounts of about 3–5% of total cellular protein in S. lividans. As another derivative construct, expression of NS1 and galK was achieved by inserting a coding sequence for the influenza virus protein NS1 derived from pAPR801 (Young et al., in the The Origin of Pandemic Influenza Viruses, 1983, ed. W. G. Laver, Elsevier Science Publishing Company) between the galK gene and the XP55 promoter, the promoter being on a 750 bp Sal I-Bgl II (3.7) fragment. In other derivative constructs, the NS1 coding sequence was fused to the cII ribosome binding site and expressed from a Sal I-Bgl II (3.7) fragment, the Sal I site being about 300 bp downstream of the Bgl II (2.7) site, and the NS1 coding sequence was cut with Bam HI to remove the NS1 translation initiation codon and was fused directly to the XP55 translation initiation codon in pIJ101 and SCP2 vectors. The levels of expression were higher in the pIJ101 vectors. Finally, the Bam HI-cleaved NS1 coding sequence was fused to the Bgl II (3.7) site in the XP55 coding sequence to express NS1 intracellularly as well as a larger putative fusion protein. Significant amounts of NS1 were not detected extracellularly from this construct.

EXAMPLE 4

XP55 was isolated and analyzed for amino acid composition using a Beckman 6300 amino acid analyzer. The actual amino acid composition, alongside the composition predicted from the DNA sequence are reported in the following table:

| Amino Acid | Predicted Number | Actual Number |
|---|---|---|
| alanine | 64 | 61.7 |
| cystine | 1 | 1.2 |
| aspartic acid/ asparagine | 51 | 61 |
| glutamic acid/ glutamine | 30 | 40 |
| phenylalanine | 14 | 15.8 |
| glycine | 55 | 55 |
| histidine | 7 | 8.6 |
| isoleucine | 13 | 14.4 |
| lysine | 23 | 26.9 |
| leucine | 42 | 41.7 |
| methionine | 4 | 4.2 |
| proline | 32 | 37.1 |
| arginine | 40 | 40 |
| serine | 22 | 22 |
| threonine | 40 | 35 |
| valine | 34 | 36.1 |
| tryptophan | 6 | — |
| tyrosine | 19 | 18.4 |
| unknown | 2 | — |

Streptomyces lividans strains 1326 and 1326-9 and a strain containing pIJ6 are publicly available from various sources. To further ensure availability, these strains have been deposited with the Agricultural Research Culture Collection in Peoria, Ill. on June 1, 1982, without restrictions on availability, and assigned accession numbers 15091, 15090 and 15092, respectively.

While the above description is illustrative of the invention and of the preferred embodiments thereof, the invention is not limited to the precise embodiments illustrated herein, but rather includes all modifications thereof coming within the scope of the following claims. In particular, the invention is not limited to fragments having restriction endonuclease sites or DNA sequences as illustrated, inasmuch as such sites and sequences can vary or be varied without materially affecting the invention.

What is claimed is:

1. A plasmid comprising the Streptomyces XP55 gene.
2. A plasmid comprising the promoter of the Streptomyces XP55 gene, not linked to the XP55 structural gene.
3. A microorganism transformed with the plasmid of claim 1.
4. The microorganism of claim 3 which is a Streptomyces.
5. A microorganism transformed with the plasmid of claim 2.
6. The microorganism of claim 5 which is a Streptomyces.
7. A fused gene comprising the excretion signal of the Streptomyces XP55 gene fused to a heterologous coding sequence.
8. A plasmid comprising the fused gene of claim 7.
9. A microorganism transformed with the plasmid of claim 8.
10. The microorganism of claim 9 which is a Streptomyces.

* * * * *